US00RE33988E

United States Patent [19]

Evans

[11] E Patent Number: Re. 33,988

[45] Reissued Date of Patent: Jul. 7, 1992

[54] DIETARY SUPPLEMENTATION WITH ESSENTIAL METAL PICOLINATES

[75] Inventor: Gary W. Evans, Puposky, Minn.

[73] Assignee: The United States of America as repesented by the Secretary of Agriculture, Washington, D.C.

[21] Appl. No.: 484,549

[22] Filed: Feb. 26, 1990

Related U.S. Patent Documents

Reissue of:

[64] Patent No.: 4,315,927
Issued: Feb. 16, 1982
Appl. No.: 176,234
Filed: Aug. 8, 1980

[51] Int. Cl.[5] ..... A61K 31/555
[52] U.S. Cl. ..... 514/188; 514/184
[58] Field of Search ..... 514/188

[56] References Cited

U.S. PATENT DOCUMENTS

| | | | |
|---|---|---|---|
| 2,974,043 | 3/1961 | Hockberg et al. | 424/266 |
| 4,020,158 | 4/1977 | Ashmead | 424/177 |
| 4,021,569 | 5/1977 | Abdel-Monem | 424/289 |
| 4,167,564 | 9/1979 | Jensen | 424/177 |

OTHER PUBLICATIONS

Kratky—Chem. Abst. vol. 80 (1974), p. 91239a.
Pallauf et al.—Chem. Abst. vol. 79 (1973), p. 124941 h.
Kassen et al.—Chem. Abst. vol. 82 (1975), p. 64438 z.
Chylik et al.—Chem. Abst. vol. 45 (1951), p. 6348 H.
Evans—Fed. Proceed., vol. 38, p. 703, Abst. No. 2501, Mar. 1979.
Evans—Nutrition Reviews, vol. 38(4), pp. 137-141, Apr. 1980.
Krieger—Nutrition Reviews, vol. 38(4), pp. 148-150, Apr. 1980.
G. W. Evans et al., "Detection of Labile Zinc-Binding Ligands in Biological Fluids" *Analytical Chemistry* 51:839-843 (Jun. 1979).
G. W. Evans "Review of Studies with Chromium Picolinate in Humans," Nutrition Report, Oct., 1989.
Y. Kidana, M. Noji, H. Koike, "Studies on Nicotinic Acid and Isonicotimic Acid Metal Complexes," *J. of Pharmaceutical Society of Japan* 93:129-1273 (1973).
R. Paul, et al. "Metal Complexes of Ethyl Picolinate," *J. of Inorg. Nucl. Chem.*, vol. 36:3703-3707 (1974).
Hahn & Evans, *Am. J. Phsiology*, 228:1020-1023 (1975).
P. Lumme, et al. "The Crystal Structure of Zinc Binding Ligands . . . " *Analytic Chemistry* vol. 51 3011-3022 (Jun. 1979).
M. Menard, R. Cousins, "Effect of Citrate Glutathione and Picolinate on Zinc Transport," *J. of Nutrition* 113:1434-1442 (1983).
W. Mertz, M.D., "Effects and Metabolism of Glucose Tolerance Factor," *Nutrition Reviews* vol. 33:129-135, (1975).
A. Prasad, D. Oberleas, "Binding of Zinc to Amino Acids and Serum Proteins in Vitro," *J. of Laboratory and Clinical Medicine* vol. 76:416-425 (1970).
R. Raffaniello, R. Wapnir, "Zinc Liptake by Isolated Rat Enterocytes: Effect of Low Molecules Weight Ligands." *P.S.G.B.M.* vol. 192:219-224 (1989).
P. Johnson, G. Evans, "Source of Maternal Milk Zinc for Absorption by Suckling Rats," *Proc. of the Soc. for Exper. Biol. & Medicine*, 163:372-375 (1980).
H. Roth, M. Kirchgessner, "Utilization of Zinc from Picolinate or Citric Acid Complexes in relation to Dietary Protein Source in Rats," American Institution of Nutr. (1985).
C. J. Seal, F. W. Heaton, "Chemical Factors Affecting the Intestinal Absorption of Zinc in Vitro and in Vivo," *Brit. J. of Nutr.*, vol. 50:317-324 (1983).
R. Wapnir & L. Stiel, "Zinc Intestinal Absorption in Rats: Specificity of Amino Acids as Ligands," *J. of Nutrition* vol. 116: 2171-2179 (1986).
I. Krieger & G. W. Evans, "Acrodermatitis enteropathica without hypozincemiz: Therapeutic effect of a pancreatic enzyme preparation due to a zinc-binding ligand," J. Pediatrics 96(1): 32-33 (Jan. 1980).
I. Krieger & G. W. Evans, "A variant of Acrodermatitis enteropathica (AE) without hypozincemia. Therapeutic effect of pancreatic enzyme due to a zinc binding ligand," J. Nutr. 109: xxi, Abstract No. 19 (Jun. 1979).
G. W. Evans et al., "Purification and characterization of a zinc-binding ligand in rat intestine," J. Nutr. 109: xxxii, Abstract No. 89 (Jun. 1979).

*Primary Examiner*—Sam Rosen
*Attorney, Agent, or Firm*—M. Howard Silverstein; John D. Fado; Curtis P. Ribando

[57] ABSTRACT

The levels of essential metals in the mammalian system can be precisely controlled by administering these metals in the form of exogenously synthesized coordination complexes of picolinic acid. The complexes are characterized by the following structural formula:

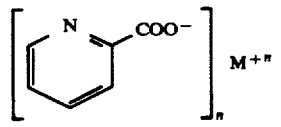

wherein M represents the metallic cation and n is equal to the cation's valence.

21 Claims, No Drawings

DIETARY SUPPLEMENTATION WITH ESSENTIAL METAL PICOLINATES

Matter enclosed in heavy brackets [ ] appears in the original patent but forms no part of this reissue specification; matter printed in italics indicates the additions made by reissue.

BACKGROUND OF THE INVENTION

1. Field of the Invention

The assimilation of an adequate quantity of physiologically important heavy metals is essential to the health of both humans and animals. Failure of the body to ingest and absorb the necessary amounts of such metals can lead to improper functioning of the metabolic processes as well as to a variety of diseases and associated symptoms. For example, anemia is correlated with an iron deficiency. Inadequate amounts of zinc may lead to skin conditions, loss of taste, neuropsychiatric symptoms, and in some animals the development of congenital anomalies and even the suppression of growth.

The absorptive cells of the mammalian intestine contain membranes and metal-binding proteins that present an ominous barrier to the transport of essential metal ions from the lumen to the blood. While metal deficiencies are often associated with improper dietary intake, they are also likely to be the result of malabsorption through this barrier. For instance, the infant disease acrodermatitis enteropathica (AE) impedes zinc absorption in the body, leading to death if not timely checked. This invention relates to a novel method of supplementing the diets of humans and animals with essential metals in an assimilable form which compensates for certain absorptive disorders.

2. Description of the Prior Art

Elemental metal and inorganic metallic salts have generally proven to be ineffective dietary amendments, particularly for subjects having intestinal malfunctions. Pharmacological doses of one metal can cause side effects resulting from competition with other metals. Also, the toxicity of these forms often restricts the dosages to suboptimal levels for attaining the desired profile in the organism's system.

More recent attempts to correct for metal deficiencies have concentrated on the use of organometallic compounds. Braun et al. [Europ. J. Pediat. 121: 247-261 (1976)] describes an attempt to treat AE in two children with 20 mg. Zn daily in the form of zinc-DL-aspartate, but with absolutely no clinical improvement. Ashmead et al., U.S. Pat. No. 4,020,158, employs metal proteinates as a feed supplement in which hydrolyzed protein products are chelated with metal ions under carefully controlled reaction conditions. Similarly, in U.S. Pat. No. 4,167,564, N. L. Jensen shows administering to animals essential metals as complexes or chelates with hydrolyzed proteins, wherein the complexes are stabilized by means of a buffer system. M. M. Abdel-Monem, U.S. Pat. No. 4,021,569, teaches zinc supplementation via zinc methionine complex salts.

While there is evidence that metals complexed with protein derivatives are more effectively assimilated than the elemental or inorganic salt forms, the exact mechanism of absorption, particularly as related to competing metals, has never been previously elucidated. Accordingly, there has always been some uncertainty attached to the prescription of proper dosages of supplemental elements.

SUMMARY OF THE INVENTION

I have now discovered that when selected essential metals as administered to mammals as exogenously synthesized coordination complexes of picolinic acid, they are directly available for absorption into the system without competition from other metals.

In accordance with this discovery, it is an object of the invention to provide a composition and method for selectively supplementing the essential metals in the diets of humans and mammalian animals, and for facilitating absorption of these metals by the intestinal cells.

It is also an object of the invention to correct predetermined metal deficiencies in mammals and to eliminate the symptoms of those deficiencies without concurrently reducing the assimilated levels of other essential metals.

Another object of the invention is to administer trace elements in a safe, physiological form; that is, in the same form endogenously produced and utilized by the normal mammalian body. By so doing, deficiencies can be therapeutically eliminated without the need for pharmacological doses of metals, even when caused by intestinal malabsorption problems.

A further object of the invention is to administer supplemental metals in a form which is simple to produce and economically feasible to distribute on a commercial basis.

Other objects and advantages of this invention will become readily apparent from the ensuing description.

DETAILED DESCRIPTION OF THE INVENTION

The term "exogenously synthesized" as used herein is intended to distinguish the complexes of the invention from those which are endogenously produced by the body. The exogenously synthesized essential metal coordination complexes of picolinic acid (pyridine-2-carboxylic acid) for use in this invention are characterized by the following structural formula:

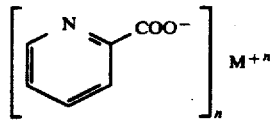

wherein M represents the metallic cation and n is equal to the cation's valence. The anionic picolinate moiety acts as a strong bidendate chelating agent, or ligand, capable of binding the cation. The cation may be any bivalent or trivalent metallic trace element essential to the nutritional well-being of humans or other mammalian species, provided that it exhibits a binding capacity with picolinic acid, as readily determined by a person in the art. Of particular interest are zinc, iron, and chromium, though it is envisioned that others such as copper, cobalt, and manganese would also be operable. These complexes are prepared by the simple method of adding picolinic acid to an aqueous solution of a water-soluble salt of the desired metal. Illustrative salts without limitation thereto are the sulfates, chlorides, and nitrates. In most cases the picolinates will crystallize from solution within about 24 hours under ambient conditions. However, it may be desirable to reduce the temperature in order to hasten precipitation. The product may be purified by recrystallization, and then recovered and dried by any conventional procedure.

While the coordination complexes of this invention are intended primarily for oral ingestion, it is envisioned that they may also be injected directly into the gastrointestinal tract. When administered orally, they will generally be incorporated in the food material or drinking water. Alternatively, they may be manufactured into tablets or pills with a suitable diluent or carrier using any known technique.

The metal picolinates may be administered singly or in any combination. Insofar as the complexed cations are substantially 100% available to the mammalian system, supplementation may be limited to physiological amounts; that is, the quantity of metal which will actually be utilized by the body. In the case of a partial deficiency, the supplement need only contain a complementary amount of the deficient metal. For example, if the daily requirement of zinc were 5 mg. and the body was otherwise assimilating 2 mg., then an additional 3 mg. of zinc would be administered daily as zinc picolinate. For purposes of this invention, any dosage which will raise the metal level in the mammalian system to a predetermined value will be considered an effective amount or an effective dose.

While the applicant does not wish to be bound to any particular theory, it appears that when a metal is administered as the exogenously synthesized picolinate complex, it is transported from the intestinal lumen into the plasma by the same mechanism as dietary metal which is ligated in the intestinal tract by endogenous picolinic acid. The correlation between endogenous picolinic acid and zinc absorption has been previously reported by G. W. Evans et al. [Federal Proceedings 38: 703 (March 1979)] and G. W. Evans [Nutrition Reviews 38: 137-141 (1980)]. It now appears that when picolinic acid ligates other essential metals, it facilitates their absorption as well, even when exogenously synthesized. The primary advantage of the exogenous supplements of the invention is that they permit precise, preselected control over assimilation of the desired metals, and they are essentially immune to competition from other metals. An incidental and unexpected advantage is that by supplying exogenously synthesized picolinate complexes of one element, additional endogenous picolinic acid is sometimes available for facilitating the absorption of other dietary elements, thereby enhancing the overall essential metal profile of the system. Because the compounds of the invention have physiological counterparts, there is little question of their safety.

The following examples are intended only to further illustrate the invention and are not intended to limit the scope of the invention which is defined by the claims.

EXAMPLE 1

Preparation of Zinc Picolinate

Thirty grams of $ZnSO_4.7H_2O$ was dissolved in 200 ml. deionized water at room temperature. Thereafter, 20 g. picolinic acid (Sigma Chemical, St. Louis, MO) was added to the solution and the solution was stirred continuously. Within 3-5 minutes a precipitate began to form. After 30 minutes the stirring was discontinued and the mixture was left standing at room temperature until the precipitate had settled to the bottom. The supernatant was removed by aspiration and the precipitate was suspended in enough deionized water to yield 200 ml. This suspension was then heated in a beaker with continuous stirring until the precipitate had completely dissolved after which the beaker was placed in an ice bath and stored overnight in a cold room (4°). The following morning the supernatant was aspirated from the crystals and the crystals were freeze dried. Assay of the crystals proved that the complex contained 2 moles of picolinic acid and 1 mole of zinc [zinc dipicolinate, $Zn(PA)_2$].

EXAMPLE 2

Preparation of Copper Picolinate

The procedure of Example 1 was repeated except that $CuSO_4.5H_2O$ was substituted for the zinc sulfate and recrystallization was facilitated by dissolving only small fractions of the precipitate in hot water at a time. The conversion of copper dipicolinate [$Cu(PA)_2$] was approximately 100%.

EXAMPLE 3

Preparation of Ferrous Picolinate

The procedure of Example 1 was repeated except for the following. Twenty grams of $FeSO_4.7H_2O$ was substituted for the zinc sulfate. When the picolinic acid was added, the solution turned red. The precipitate was recrystallized by dissolving it in 200 ml. of deionized boiling water followed by cooling in an ice bath. The ferrous dipicolinate [$Fe(PA)_2$] product was air dried.

EXAMPLE 4

Preparation of Chromium Picolinate

A solution was prepared by dissolving 512 mg. $CrCl_3.6H_2O$ (100 mg. Cr) and 750 mg. picolinic acid in 4.0 ml. deionized water. Crystals of chromium tripicolinate [$Cr(PA)_3$] formed after about 24 hours.

EXAMPLE 5

Zinc Supplementation of Pregnant and Lactating Dams

Female rats of the Long-Evans strain were bred and then transferred to individual stainless steel cages. They were fed Purina Lab Chow (Ralston Purina Co., St. Louis, MO) and deionized water for the first 14 days of gestation. Thereafter, the females were transferred to individual solid plastic cages and were fed ad libitum a purified basal diet (Table I) and a water solution that contained either zinc picolinate (10 μg. Zn/ml.) or zinc acetate (10 μg. Zn/ml.). The basal diet contained 8.5 μg. Zn/g. and 2 μg. pyridoxine-HCl/g.

Immediately after the pups were born, litter sizes were reduced to eight and these pups nursed for 5 days. At 1000 hours on the morning of the fifth day after birth, the pups were decapitated. The liver and kidneys were removed and freeze dried. The zinc concentration of these organs was determined by atomic absorption spectrometry (Varian, Model 1250) after the tissues had been digested in a mixture of nitric and sulfuric acids.

During the last week of gestation and the 5 days of lactation, there was no significant difference in either food consumption or supplemented water consumption between dams given zinc acetate and dams given zinc picolinate. Food consumption was 17.5±1.2 g./day for the dams in both groups. The dams given water supplemented with zinc acetate consumed 33.5±3.5 ml./day while the dams given the zinc picolinate supplement consumed 35.1±2.8 ml./day.

As shown in Table II, the zinc concentration of both the liver and the kidneys was significantly greater from the pups suckling dams given the zinc picolinate supplement, indicating that zinc complexed with picolinic acid is transferred from the intestine of the lactating female to the pups much more readily than an organic zinc salt.

TABLE I

Composition of the Basal Diet

| Ingredient | g./kg. |
|---|---|
| Sucrose[a] | 624.6 |
| Vitamin-free casein[b] | 200 |
| Corn oil[c] | 90 |
| Zinc-free salt mix[d] | 26.9 |
| Fibrous cellulose powder[e] | 40 |
| Vitamin ADE mix[f] | 10 |
| Rat vitamin mix[g] | 5 |
| Methionine[h] | 2 |
| Choline chloride[h] | 1.5 |

[a]Jack Frost, National Sugar Refining Co., Philadelphia, PA.
[b]Teklad Test Diets, Madison, WI.
[c]Mazola, Best Foods, Englewood Cliffs, NJ.
[d]Bernhurt and Tomarelli salt mixture with zinc omitted[J. Nutr. 89: 495-500(1966)]. Specially prepared Teklad Test Diets. The zinc content of the basal diet was 8.5 μg. Zn/g.
[e]Whatman CFII, W. and R. Balston Ltd., London, England.
[f]Vitamins were purchased from Nutritional Biochemicals Corp. The vitamin ADE mix contained 5.75 mg. ergocalciferol, 10 g. α-tocopherol, 2 g. retinyl palmitate, and corn oil to give a total weight of 1000 g.
[g]The rat vitamin mix contained 8 g. nincinamide, 5 g. calcium pantothenate, 1.6 g. riboflavin, 800 mg. thiamine hydrochloride, 400 mg. pyridoxine-HCl, 200 mg. folic acid, 30 mg. cyanocobalamine, 20 mg. menadione and sucrose to a final weight of 1000 g.
[h]Grand Island Biochemical Co., Grand Island, NY.

TABLE II

Zinc Concentration of Liver and Kidneys from Pups Nursing Dams Fed Zinc Supplement

| Supplement to dam | Liver, μg. Zn/g. dry wt. | Kidneys, μg. Zn/g. dry wt. |
|---|---|---|
| Zinc acetate (n = 40)[a] | 221 ± 52 | 92 ± 20 |
| Zinc picolinate (n = 56) | 276 ± 63[b] | 125 ± 30[b] |

[a]Number of pups shown in parenthesis. All values are mean ± S.D.
[b]Significantly greater ($P < 0.01$) than value obtained from pups nursing dams given the zinc acetate supplement. (Student's t-test).

EXAMPLE 6

The following clinical study has been reported in detail by I. Krieger in Nutrition Reviews 38(4): 148-150 (April 1980), herein incorporated by reference.

A 1-year-old human female suffering from the time that breastfeeding was stopped at 4 months from a variant form of acrodermatitis enteropathica, in which there was zinc dependency without hypozincemia, was maintained substantially symptom-free on an elemental zinc supplement of 45 mg./day until 20 months. During the few months which followed, intermittent treatments were interspersed with periods of reoccurring symptoms. At approximately 2 years, the patient was started on 60 mg. $Zn^{++}$ (as zinc sulfate) and remained symptom-free for more than 2 years. Two attempts to lower the dosage to 30 mg. $Zn^{++}$/day were unsuccessful because of recurrent diarrhea.

At 4 years, she was started on 23.7 mg. zinc dipicolinate per day, diluted in water and divided into two doses of 5 ml. each. This amount of zinc dipicolinate contains 5 mg. $Zn^{++}$ which is equivalent to the average intake of normal age controls. Assuming that the patient received a similar quantity of zinc in her diet, the total intake would have been 65 mg. $Zn^{++}$ when on the zinc sulfate diet, and 10 mg. $Zn^{++}$ during treatment with the picolinate. After 5 months, the patient remained symptom-free. Plasma zinc levels varied with the treatment as follows:

| Treatment | Plasma zinc value (μg./deciliter) |
|---|---|
| none | 120 |
| $ZnSO_4$ | 172 |
| $Zn(PA)_2$ | 148 |

An incidental and unexpected result was an increase in plasma copper level from 155 μg./deciliter during $ZnSO_4$ treatment to 251 μg./deciliter after 10 weeks of treatment with the picolinate. This is probably explainable on the basis that additional free intestinal picolinic acid was available to complex with the copper and thereby enhance its absorption.

EXAMPLE 7

A 42-year-old human female having a history of iron deficiency anemia and suffering from exhaustion had been nonresponsive to pharmacological doses (about 60 mg./day or more) of iron in commercially available iron supplements. Blood analysis revealed a hematocrit of 31% and hemoglobin of 10.3 g./dl. She was started on 30 mg. ferrous dipicolinate per day. This supplement contained 5 mg. of elemental iron and was administered by mixing the powdered complex with a morning cup of coffee. During the course of supplementation she stated that she felt extremely energetic and after 12 days, her hematocrit increased to 36% and her hemoglobin increased to 12 g./dl. Discontinuation of the supplement on the 29th day led to a decrease in hemoglobin to 11.5 g./dl. These observations suggest that ferrous picolinate can effectively improve the iron profile in humans when administered at physiological levels.

It is understood that the foregoing detailed description is given merely by way of illustration and that modification and variations may be made therein without departing from the spirit and scope of the invention.

I claim:

1. A food composition for selectively supplementing essential metals in a mammalian diet and for facilitating absorption of said metals by the mammalian system comprising a food composition containing an effective amount of at least one exogenously synthesized essential metal picolinate complex characterized by the following structural formula:

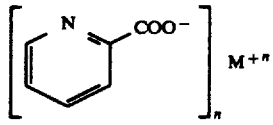

wherein M represents the metallic cation and n is equal to the cation's valence, *whereby said exogenously synthesized essential metal picolinate complex is supplemental to any endogenous essential metal picolinate present in said composition.*

2. The composition as described in claim 1 wherein said essential metal picolinate complex is zinc picolinate.

3. The composition as described in claim [1] *20* wherein said essential metal picolinate complex is ferrous picolinate.

4. A method for selectively supplementing essential metals in a mammalian diet and for facilitating absorption of said metals by the mammalian system comprising administering to said mammal an effective amount of an exogenously synthesized essential metal picolinate complex characterized by the following structural formula:

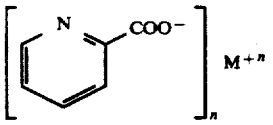

wherein M represents the metallic cation and n is equal to the cation's valence, *whereby said exogenously synthesized essential metal picolinate complex is supplemental to any endogenous essential metal picolinate present in said composition.*

5. The method as described in claim 4 wherein said essential metal picolinate complex is administered orally.

6. The method as described in claim 5 wherein said essential metal picolinate complex is administered as an aqueous solution.

7. The method as described in claim 5 wherein said essential metal picolinate complex is administered in combination with a food material.

8. The method as described in claim 4 wherein said essential metal picolinate complex is zinc picolinate.

9. The method as described in claim [4] *21* wherein said essential metal picolinate complex is ferrous picolinate.

10. The method as described in claim 4 wherein said mammal is a human.

11. The method as described in claim 4 wherein said mammal is a domesticated animal.

*12. A food composition for selectively supplementing an essential metal selected from the group consisting of iron, chromium, copper, cobalt, and manganese in a mammalian diet and for facilitating absorption of said metal by the mammalian system comprising a food composition containing an effective amount of at least one exogenously synthesized essential metal picolinate complex characterized by the following structural formula:*

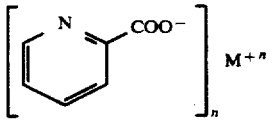

*wherein M represents the cation of said metal and n is equal to the cation's valence.*

*13. The composition as described in claim 12 wherein said essential metal picolinate complex is chromium picolinate.*

*14. The composition as described in claim 12 wherein said essential metal picolinate complex is copper picolinate.*

*15. The composition as described in claim 12 wherein said essential metal picolinate complex is cobalt picolinate.*

*16. The composition as described in claim 12 wherein said essential metal picolinate complex is manganese picolinate.*

*17. A method for selectively supplementing an essential metal selected from the group consisting of iron, chromium, copper, cobalt, and manganese in a mammalian diet and for facilitating absorption of said metal by the mammalian system comprising administering to said mammal an effective amount of an exogenously synthesized essential metal picolinate complex characterized by the following structural formula:*

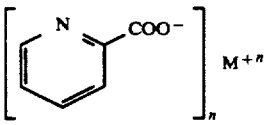

*wherein M represents the cation of said metal and n is equal to the cation's valence.*

*18. The method as described in claim 17 wherein said essential metal picolinate complex is chromium picolinate.*

*19. The method as described in claim 17 wherein said essential metal picolinate complex is copper picolinate.*

*20. The method as described in claim 17 wherein said essential metal picolinate complex is cobalt picolinate.*

*21. The method as described in claim 17 wherein said essential metal picolinate complex is manganese picolinate.*

* * * * *